(12) United States Patent
Gaugler et al.

(10) Patent No.: US 11,470,820 B2
(45) Date of Patent: Oct. 18, 2022

(54) NON-MEMBRANE FEEDING DEVICE AND DIET FORMULATION FOR MOSQUITO COLONY PRODUCTION

(71) Applicant: RUTGERS, THE STATE UNIVERSITY OF NEW JERSEY, New Brunswick, NJ (US)

(72) Inventors: Randy Gaugler, North Brunswick, NJ (US); Devi S. Suman, Highland Park, NJ (US); Kshitij Chandel, Highland Park, NJ (US); Yi Wang, South River, NJ (US)

(73) Assignee: Rutgers, The State University of New Jersey, Piscataway, NJ (US)

( * ) Notice: Subject to any disclaimer, the term of this patent is extended or adjusted under 35 U.S.C. 154(b) by 852 days.

(21) Appl. No.: 16/331,820

(22) PCT Filed: Sep. 8, 2017

(86) PCT No.: PCT/US2017/050778
§ 371 (c)(1),
(2) Date: Mar. 8, 2019

(87) PCT Pub. No.: WO2018/049229
PCT Pub. Date: Mar. 15, 2018

(65) Prior Publication Data
US 2019/0246608 A1 Aug. 15, 2019

Related U.S. Application Data

(60) Provisional application No. 62/385,125, filed on Sep. 8, 2016.

(51) Int. Cl.
*A01K 29/00* (2006.01)
*A01K 67/00* (2006.01)
(Continued)

(52) U.S. Cl.
CPC .............. *A01K 29/00* (2013.01); *A01K 67/00* (2013.01); *A01K 67/033* (2013.01);
(Continued)

(58) Field of Classification Search
CPC ...... A01K 29/00; A01K 67/00; A01K 67/033; A23K 20/147; A23K 20/158;
(Continued)

(56) References Cited

U.S. PATENT DOCUMENTS 5,133,289 A 7/1992 Georgi
8,133,524 B1 3/2012 Acar et al.
(Continued)

OTHER PUBLICATIONS

International Search Report, dated Nov. 14, 2017, issued in corresponding International Application No. PCT/US2017/050778, filed Sep. 8, 2017.
Allan, Sandra A. et al., "Laboratory evaluation of lactic acid on attraction of Culex spp. (Diptera: Culicidae)," Journal of Vector Ecology, vol. 35, No. 2, Jun. 2010, pp. 318-324.
(Continued)

*Primary Examiner* — Trevor Love
(74) *Attorney, Agent, or Firm* — Kathleen D. Rigaut; Howson & Howson LLP

(57) ABSTRACT

An artificial feeding system for maintenance and growth of hematophagous insects is disclosed to comprise a blood-free diet formulation and a feeding device. The blood-free diet formulation comprises effective amounts of a protein source and a carbohydrate source, wherein the blood-free diet formulation is suitable for egg production and colony maintenance of hematophagous insects. The feeding device comprises a diet reservoir for receiving the blood-free diet formulation and a feeding platform for hematophagous insects to feed the blood-free diet formation from the diet reservoir.

20 Claims, 15 Drawing Sheets

(51) Int. Cl.
  *A01K 67/033* (2006.01)
  *A23K 20/147* (2016.01)
  *A23K 20/158* (2016.01)
  *A23K 20/163* (2016.01)
  *A23K 50/90* (2016.01)

(52) U.S. Cl.
  CPC .......... *A23K 20/147* (2016.05); *A23K 20/158* (2016.05); *A23K 20/163* (2016.05); *A23K 50/90* (2016.05); *A23V 2002/00* (2013.01); *A23V 2250/5436* (2013.01); *A23V 2250/606* (2013.01); *A23V 2250/61* (2013.01); *A23V 2250/628* (2013.01)

(58) Field of Classification Search
  CPC .. A23K 20/163; A23K 50/90; A23V 2002/00; A23V 2250/5436; A23V 2250/606; A23V 2250/60; A23V 2250/628

See application file for complete search history.

(56) References Cited

U.S. PATENT DOCUMENTS

2007/0169209 A1    7/2007  Hoffman et al.
2012/0148705 A1    6/2012  Acar et al.

OTHER PUBLICATIONS

Gonzales, Kristina K. et al., "Blood serum and BSA, but neither red blood cells nor hemoglobin can support vitellogenesis and egg production in the dengue vector Aedes aegypti," PeerJ, vol. 3, May 2015, e938, pp. 1-14.

Hosoi, Teruhiko, "Identification of blood components which induce gorging of the mosquito," Journal of Insect Physiology, vol. 3, No. 3, Oct. 1959, pp. 191-218.

Kogan, P. H., "Substitute blood meal for investigating and maintaining Aedes aegypti (Diptera: Culicidae)," Journal of Medical Entomology, vol. 27, No. 4, Jul. 1990, pp. 709-712.

Phasomkusolsil, Siriporn et al., "Maintenance of mosquito vectors: effects of blood source on feeding, survival, fecundity, and egg hatching rates," Journal of Vector Ecology, vol. 38, No. 1, Oct. 2013, pp. 38-45.

Pitts, R. Jason, "A blood-free protein meal supporting oogenesis inthe Asian tiger mosquito, *Aedes albopictus* (Skuse)," Journal of Insect Physiology, vol. 64, Mar. 2014, pp. 1-6.

NON-MEMBRANE FEEDING DEVICE AND DIET FORMULATION FOR MOSQUITO COLONY PRODUCTION

CROSS-REFERENCE TO RELATED APPLICATIONS

This application is a § 371 of International Application No. PCT/US2017/050778, filed Sep. 8, 2017, which claims priority from U.S. provisional patent application Ser. No. 62/385,125, entitled "A non-membrane feeding device and diet formulation for mosquito colony production", filed Sep. 8, 2016. The entire disclosure of each of the aforesaid applications is incorporated by reference in the present application.

FIELD OF THE INVENTION

This invention relates to the fields of mosquito maintenance and propagation. More specifically a non-membrane feeding device and diet formulation for mosquito colony production is disclosed.

BACKGROUND OF THE INVENTION

Numerous publications and patent documents, including both published applications and issued patents, are cited throughout the specification in order to describe the state of the art to which this invention pertains. The disclosure of each of these citations is incorporated herein by reference as though set forth in full.

Up to 700 million people are infected and more than a million die each year from mosquito-borne illnesses (Caraballo, Hector (May 2014)). Several diseases transmitted by mosquitoes are malaria, dengue, filariasis, West Nile virus, chikungunya, yellow fever, etc. The next generation of mosquito control technologies seem unlikely to require unilateral use of the toxic chemicals that have been dominate over the past 75 years. The new ecologically benign technologies currently being devised are increasingly focused on genetically modified or sterile mosquitoes, methods that require production of massive numbers of mosquitoes for field release. Female mosquitoes generally require a blood meal to develop eggs for the next generation. Mosquitoes are divergent in host preference, which include humans, animals, birds, reptiles, and amphibians. They also vary in daily rhythms of blood feeding such as diurnal, nocturnal and crepuscular etc. In a laboratory setup, cultures are maintained mostly with a blood feeding system, where female mosquitoes are fed with vertebrate blood. This approach has certain drawbacks. While the diet rich is in protein, diets based on vertebrate blood are expensive, inconsistent in quality, and require pathogen-free certification. Moreover, such blood based diets are unstable during storage. Indeed, the blood must be maintained at 37° C. and most approaches require a membrane to mimic vertebrate skin for the mosquito to pierce. Laboratories maintaining mosquito colonies throughout the world are dependent on live animals or animal blood. Hence, production of large quantities of mosquitoes for mass-release in mosquito control trials places great pressure on animal care facilities and increases maintenance costs several-fold. The blood for these systems usually comes from live animals or birds, which are under constant surveillance and ethical regulations, requiring stringent animal care. Consequently, a laboratory maintaining only a small number of mosquito cages expends thousands of dollars for the blood feeding arrangements which rely on use of animals or artificial membrane feeding system. Understandably then, considerable research effort has been devoted to the development of artificial alternatives to blood. In some labs, researchers use blood components or synthetic blood-free diets based on the host-seeking and blood-feeding behavior of mosquitoes, in which case, the membrane feeding system replaces animal blood or live animals. While an artificial membrane feeding system has been developed and is available commercially (Hemotek), this system still requires the use of collected animal blood. There are huge variations in acceptability of this artificial membrane system for various mosquito species. Blood quality, age and composition also affect system performance (Phasomkusolsil et al., 2013). Often, quality blood for colony maintenance can be difficult to obtain. Some studies have used blood components or synthetic blood-free diet with the membrane feeding system to replace animal blood or live animals. These diets are based on host-seeking and blood feeding behavior of mosquitoes and contain multiple components including phagostimulants, protein sources, digestive activators, buffer solutions, attractants, etc. The performance of these diets depends entirely upon the membrane feeding system. Further, there are concerns regarding long term storage and cost effectiveness of such systems, as adenosine tri-phosphate (ATP), a widely used phagostimulant in the artificial alternatives to blood, used to encourage feeding, is expensive.

Clearly, a need exists for a commercially viable product that will replace costly, labor intensive and ethically vulnerable animal use for blood feeding and artificial membrane feeding systems.

SUMMARY OF THE INVENTION

In accordance with the present invention, an artificial feeding system for maintenance and growth of hematophagous insects is provided which exploits sugar feeding, rather than blood feeding behavior. An exemplary system comprises a diet reservoir for receiving a synthetic, blood-free diet formulation; at least one feeding platform consisting of a mosquito proof covering separating said reservoir from said platform, the system and diet formulation being suitable for egg production and colony maintenance. Another exemplary artificial feeding system comprises a blood-free diet formulation and a feeding device comprising a diet reservoir for receiving the blood-free diet formulation; and a feeding platform for hematophagous insects to sit and feed on the blood-free diet formulation from the diet reservoir. The blood-free diet formulation comprises effective amounts of a protein source and a carbohydrate source, wherein the blood-free diet formulation is suitable for egg production and colony maintenance of hematophagous insects.

In one embodiment, the system comprises a single feeding platform which is optionally a mesh. In another embodiment, the system comprises multiple feeding platforms, e.g., 2, 3, 4, 5, 6, 7, 8, 9, or 10 or more platforms. In an embodiment, the feeding platform floats over the blood-free diet formulation in the diet reservoir. In another embodiment, at least a portion of the feeding platform is hydrophobic. Yet in another embodiment, the feeding platform is a mesh.

The system can be formed from polypropylene, polyethylene, polystyrene or any other inert plastic material or a metal, such as aluminum foil, or biodegradable materials such as wax paper and the like. The feeding platform can be made of any suitable materials, including but not limited to, polystyrene, aluminum foil, wax paper, sponge, resin, wood and cardboard coated with non-wetting agents.

The diet reservoir of the system can be any shape such as circular or polygonal e.g., square, rectangular or triangular.

In another embodiment of the invention a blood free diet formulation is provided comprising effective amounts of a protein source, a carbohydrate source and, optionally a lipid source. In certain embodiments, the protein source is bovine serum albumin, egg albumin or a mixture thereof. The carbohydrate source can be glucose, sucrose, fructose, or mixtures thereof.

In certain embodiments, the lipid source is cholesterol. In a particularly preferred embodiment, the blood-free diet formulation lacks adenosine tri-phosphate, a phagostimulant and supports several different species of mosquitoes including for example, *Aedes, Anopheles* and *Culex* mosquitoes.

In another aspect of the invention, a method of maintaining and growing hematophagus insects is provided. An exemplary method comprises: (a) providing an artificial feeding system as disclosed hereinabove; (b) dissolving the blood-free diet formulation in water; and (c) feeding the hematophagus insects.

BRIEF DESCRIPTION OF THE DRAWINGS

The accompanying drawings, which are incorporated in and constitute a part of this specification, illustrate particular embodiment(s) of the invention, and together with the written description, serve to explain certain principles of the invention.

(FIG. 1A) unfed, (FIG. 1B) half fed and (FIG. 1C) full fed. Arrow shows abdominal bulging after feeding on the exemplary blood-free diet of the present invention.

(FIG. 9A) angular view, (FIG. 9B) lateral view, and (FIG. 9C) top view. Abbreviations: IP—inner feeding platform, MP—middle feeding platform, OP—outer feeding platform.

FIG. 14A shows diet feeders with flat base, a diet reservoir for holding diet and a feeding platform; FIG. 14B shows centrifuge tubes comprising exemplary diets with blue and red dyes, illuminated under UV light; and FIG. 14C shows a cup holding hungry mosquitoes and two diet feeders one with an exemplary diet comprising a red dye and the other with a blue dye.

FIG. 15A shows mosquito fed on diets with dyes under normal daylight and FIG. 15B shows similar mosquitoes under UV light (Left side—fed on blue dye diet, Center—fed on red dye diet, Right side—fed on both blue and red dye diets). Choice experiment was tested for biases using the reciprocal exchange of sugar and BSA with blue and red dyes.

FIG. 22 shows a method of maintaining and growing hematophagus insects, in accordance with various embodiments of the present invention.

DETAILED DESCRIPTION OF THE INVENTION

Reference will now be made in detail to various exemplary embodiments of the invention, examples of which are illustrated in the accompanying drawings. The following description is provided to assist the reader in understanding various embodiments and features of embodiments of the invention, and should not be considered as a limitation on the invention as disclosed herein and claimed below.

The present invention relies on a different strategy and is dependent on the sugar feeding behavior of mosquitoes thereby providing alternative pathways to mosquito host-seeking and blood feeding behaviors. Based primarily on sugar feeding behavior, the present artificial feeding system does not require a membrane feeder, phagostimulant, ATP or host chemical cues i.e. lactic acid to get the protein diet described previously (Hosoi 1959, Kogon 1990, Accar et al. 2012, Pitts 2014, Gonzales et al. 2014). The artificial feeding system of the present invention is independent of blood feeding rhythms as sugar feeding does not have any specific pattern.

As used herein unless context dictates otherwise, the term "blood-free diet" includes food compositions which preferably exclude whole blood or plasma, or serum fluids of a person or animal. The "blood-free diet" of the present disclosure may include isolated blood components, such as bovine serum albumin or hemoglobin for example. The blood-free diets of the present invention support egg production and colony maintenance of hematophagous insects. In some embodiments, the hematophagous insects are sugar feeding insects.

While the following discussion is in the context of feeding of mosquitoes, the formulations described herein, as well as the methods of determining appropriate formulations, are expected to be applicable to other hematophagous insects as well (e.g., tsetse flies, lice, bed bugs, no-see-ums, fleas, sand flies, midges, snipe flies, horse flies, stable flies, or sheep flies).

Artificial Feeding System:

In an aspect of the present disclosure, the artificial feeding system, for maintenance and growth of hematophagous insects, includes a blood-free diet formulation and a feeding device. The blood-free diet formulation comprises effective amounts of a protein source and a carbohydrate source. In such embodiments, the blood-free diet formulation is suitable for egg production and colony maintenance of hematophagous insects. The feeding system includes a diet reservoir for receiving and holding the blood-free diet formulation and a feeding platform for hematophagous insects to feed the blood-free diet formulation from the diet reservoir.

The hematophagous insects are mosquito colonies chosen from *Aedes, Anopheles, Culex* mosquitoes.

Figure 9A:
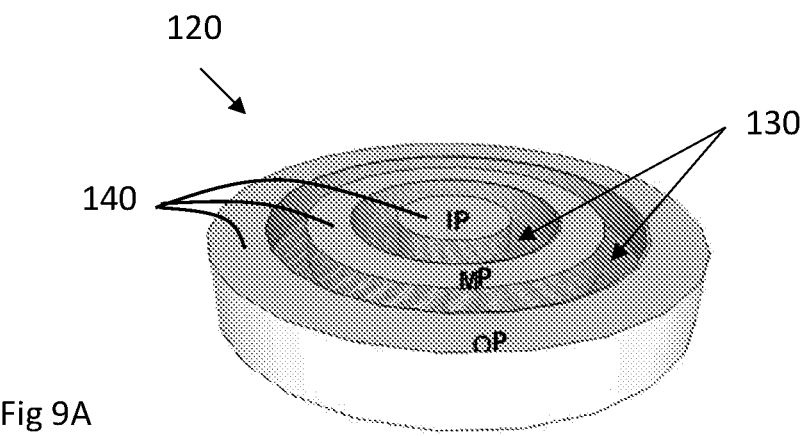
FIGS. 9A-9C shows an exemplary artificial feeding system, in accordance with various embodiments of the present invention.
Figure 9B:
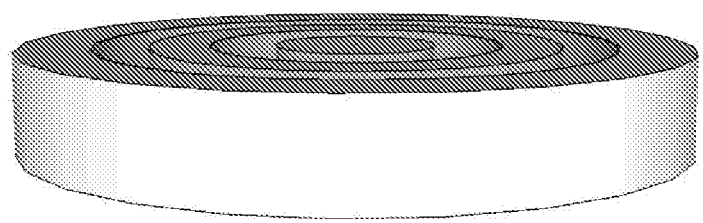
Figure 9C:
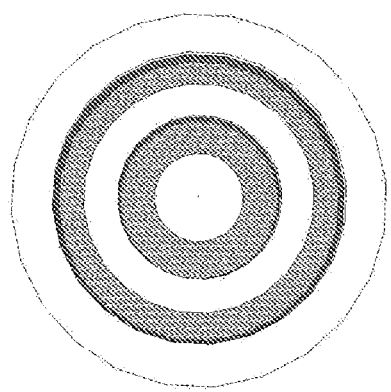

Feeding Device:

FIGS. 9A-9C shows an exemplary feeding device (120), according to various embodiments of the present invention. The feeding device (120), as shown in FIGS. 9A-9C has two parts, a diet reservoir (130) for holding the blood-free diet (not shown) and a feeding platform (140) for hematophagous insects, such as mosquitoes to sit on and feed on the blood-free diet formulation contained in the diet reservoir (130). The diet reservoir (130) is designed to provide a maximum reach of mosquitoes to diet by providing a feeding platform (140) for mosquitoes to sit in the center and on the outside edge of the periphery. In some embodiment, the feeding platform comprises a plurality of feeding platforms e.g., 2, 3, 4, 5, 6, 7, 8, 9, or 10 or more platforms. In other embodiment, the plurality of feeding platforms divide the diet reservoir into a plurality of diet reservoirs separated by the platforms. In such an embodiment, the size of the diet reservoir can be increased or reduced depending on mosquito colony size, such as by using only a portion of the plurality of diet reservoirs. For example, FIG. 9A shows an exemplary feeding device comprising two diet reservoirs and three feeding platforms: inner platform (IP), middle platform (MP) and outer platform (OP), where the two diet reservoirs are separated by the middle feeding platform. In some embodiments, the feeding device may further comprise an optional mosquito-proof covering (not shown) separating the diet reservoir from the platform. In an embodiment, the covering is a mesh made of nylon, cotton, polyester fabric or metal screen. The mosquito-proof covering can be attached to the diet reservoir using hot glue or super glue. Alternatively, the optional mosquito-proof covering can be screwed or friction fit to the diet reservoir. In some embodiment, the feeding device is free of mosquito-proof covering, and comprises only a feeding platform and a diet reservoir, on which mosquitoes can successfully feed.

Figure 22:
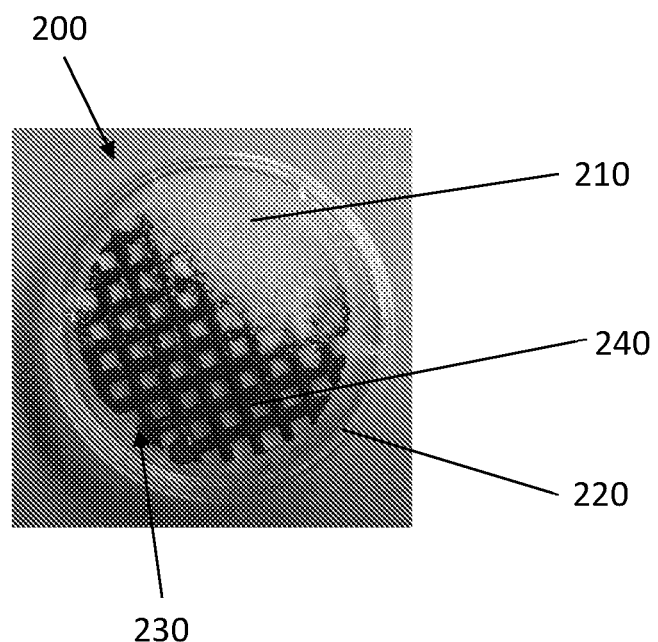
FIG. 22 shows an exemplary artificial feeding system, in accordance with various embodiments of the present invention.

FIG. 22 shows another exemplary artificial feeding system (200) comprising a blood-free diet formulation (210) and a feeding device (220), in accordance with various embodiments of the present invention. The feeding device (220) comprises a diet reservoir (230) for receiving the blood-free diet formulation and a feeding platform (240) that floats over the blood-free diet formulation in the diet reservoir. In some embodiments, at least a portion of the feeding platform is hydrophobic. In some embodiments, the feeding platform is in the form of a mesh. The feeding platform in the form of a mesh that floats, provides several advantages such as not only that the mesh can be used as a feeding platform that never gets wet, but it provides the hematophagous insects an uninterrupted and/or continuous access to the blood-free diet through the mesh as the amount of blood-free diet decreases in the diet reservoir.

The feeding device (120), (220) can have any suitable shape, including but not limited to circular or polygonal. In some embodiments, the diet reservoir is circular in shape. In another embodiment, the diet reservoir is square, triangular or rectangular in shape. In some other embodiments, the diet reservoir is annular in shape. The feeding device can have any suitable size depending upon the scale of feeding needed and the mosquito colony size, such as from 200 µL to 50 mL. In some embodiments, the diet reservoir can hold 200 µL-2 mL of diet or from 200-1000 µL; or from 1-2 mL of diet which is sufficient to feed approximately 50-100 mosquitoes. In other embodiments, the diet reservoir can hold from 10 to 50 mL of diet. Yet, in other embodiment, multiple feeding devices can be used in large scale production as alternative of larger sized device.

The diet reservoir of the feeding device can be made of any suitable material that can be formed to hold water, including but not limited to, polypropylene, polyethylene, polystyrene or any other inert plastic material or a metal, such as aluminum foil, or biodegradable materials such as wax paper and the like. The feeding platform can be made of any suitable materials, including but not limited to, polystyrene, aluminum foil, wax paper, sponge, resin, wood and cardboard coated with non-wetting agents. In some embodiments, the floating feeding platform is coated with non-wetting agents such as wax or any other hydrophobic material, to keep it from wetting, and thereby prevent feeding mosquito from getting stuck. In certain embodiments, the feeding platform is light enough to float on the liquid blood-free diet, so that it stays on top of the diet for mosquitoes to use as a feeding platform. The pore size of the mesh forming the feeding platform can be from 1×1 mm to 3×3 mm or from 1-3 mm in diameter or from ~1.5-2 mm in diameter, so that mosquito can stand on the mesh without getting stuck. In some embodiments, the pore size of the mesh forming the feeding platform is 2 mm in size, which can be diameter for circular pore or a side or diagonal for a polygonal pore.

Blood-Free Diet Formulation:

In accordance with various embodiments, the artificial feeding system of the present invention comprises a blood-free diet formulation in addition to a feeding device as disclosed hereinabove. The blood-free diet formulation of the present invention comprises effective amounts of a protein source and a carbohydrate source dispersed in a liquid, such as water (pH 7), 1 mM Phosphate Buffered Saline (PBS) (pH 7.2) or other appropriate physiological carriers suitable for egg production and colony maintenance of hematophagous insects.

The protein source present in the blood-free diet formulation can be selected from the group consisting of animal protein, milk protein, plant protein, insect protein, arthropod protein, and amino acids. In one embodiment, the protein source includes, bovine serum albumin, egg albumin, or a mixture thereof. Suitable carbohydrate sources include, but are not limited to glucose, sucrose, fructose, or mixtures thereof. The protein source can be present in an amount of 5-30% (W/V) or 10-20% (W/V) and the carbohydrate source can be present in an amount of 3-10% (W/V) or 4-8% (W/V). In a preferred embodiment, the blood-free diet formulation comprises glucose present in an amount of 5% (W/V). In another embodiment, the blood-free diet formulation comprises bovine serum albumin present in an amount of 10% (W/V).

In some embodiments, the blood-free diet formulation further comprises a lipid source, such as, for example, cholesterol. In another aspect, the blood-free diet formulation is free of a phagostimulant other than sugar. In certain embodiments, the blood-free diet formulation further comprises a traceable reagent, such as a UV dye.

Suitable examples of blood-free diet formulation, for egg development and survival of mosquitoes, include, but are not limited to:

Diet Formulations:

Diet 1: Bovine Serum albumin (5-20%) (W/V)
  Sugar (5-10%) (W/V)
  Dissolved in 1 mM Phosphate Buffered Saline (pH 7.2)
Diet 2: Bovine Serum albumin (5-10%) (W/V)
  Egg albumin (5-10%) (W/V)
  Sugar (5-10%) (W/V)
  Dissolved in 1 mM Phosphate Buffered Saline (pH 7.2)
Diet 3: Egg albumin (5-10%) (W/V)
  Sugar (5-10%) (W/V)
  Dissolved in 1 mM Phosphate Buffered Saline (pH 7.2)
Diet 4: Bovine Serum albumin (5-20%) (W/V)
  Sugar (5-10%) (W/V)
  Cholesterol (1-2 mg/ml)
  Dissolved in 1 mM Phosphate Buffered Saline (pH 7.2)
Diet 5: Bovine Serum albumin (5-20%) (W/V)
  Sugar (5-10%) (W/V)
  Dissolved in Distilled water (pH 7)

As used herein the amounts shown in % (W/V) refer to the amount of solid component in g dissolved in mL of liquid. In each formulation above, a range of 5-20% (W/V) means a range between 5, 6, 7, 8, 9, 10, 11, 12, 13, 14, 15, 16, 17, 18, 19 and 20% (W/V). A range between 5-10% (W/V) refers to any of 5, 6, 7, 8, 9, and 10% (W/V). Notably, additional components may be added to the formulations above. These include, for example, animal proteins, milk proteins, plant proteins, proteins obtained from insects or arthropods, amino acids and lipids.

In certain embodiments, the diet reservoir holding the diet composition can be placed in a warming device having a temperature range between 30 to 35° C. The present inventors have observed that warming the diet increases the success rate for the blood-free diet with respect to egg laying and survival.

Figure 23:
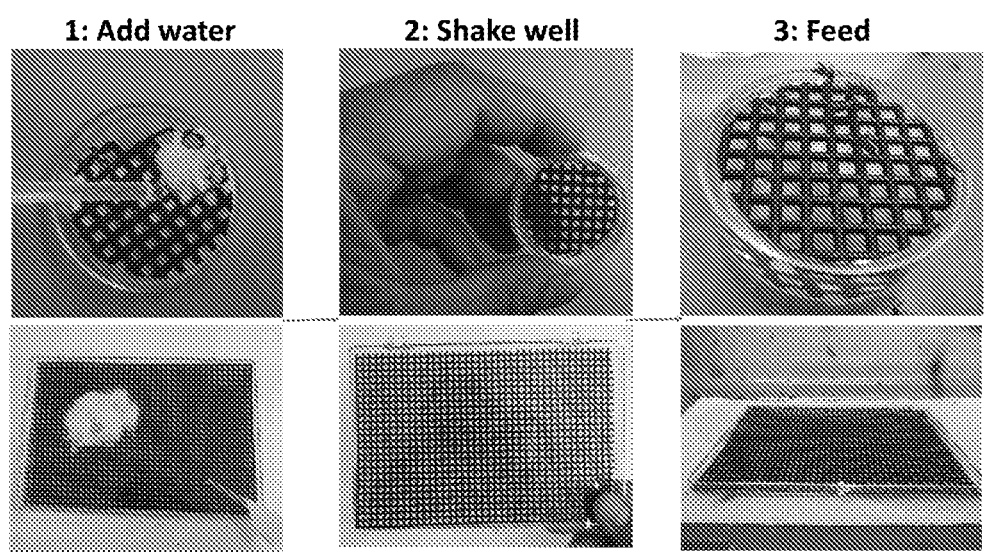
FIG. 23 shows a method of maintaining and growing hematophagus insects, in accordance with various embodiments of the present invention.

A method of maintaining and growing hematophagus insects is also provided and is shown in FIG. 23. The method comprises providing an artificial feeding system as disclosed hereinabove; adding water and shaking it well to dissolve the blood-free diet composition in water, followed by feeding the hematophagus insects. The feeding devices of the present invention provide an easy way to both prepare diet and feed mosquitoes. Furthermore, the feeding devices can have a variety of shapes and sizes, depending upon the colony size.

The device and diet composition of the present invention promotes both survival and egg laying. The blood-free diet formulations, as disclosed hereinabove are suitable for production of multiple generations of mosquitoes. The blood-free diet formulations of the present disclosure are also suitable for rearing mosquitoes under diapausing conditions and production of viable diapause eggs. The unique feeding mechanism utilizing sugar feeding behavior for mosquito egg development renders the system independent of mosquito blood feeding schedules. Moreover, the completely synthetic diet formulation is suitable for growth of a variety of different mosquito species. Furthermore, the system does not require any electrical power for operation and can be used within a broad temperature range (25° C. to 35° C.). Finally, the blood-free diet formulation of the present disclosure can be stored for longer periods of time than blood under refrigeration.

We have developed a simple blood-free diet and feeding system offering the following advances: (1) blood-free, (2) membrane-free, (3) ATP free, (4) room temperature feeding, (5) long-term storage stability even under field conditions, (6) inexpensive, (7) ease-of-handling, and (8) easy to scale-up. The key to our diet is the substitution of sugar for ATP to induce engorgement. There are two modalities in mosquito feeding: sugar and protein. Protein derived from blood supports egg production, whereas sugar derived from floral nectars supports longevity. Sugar is also an extremely potent mosquito phagostimulant. The sugar in the artificial diet described herein serves to 'fool' the mosquito into concurrently imbibing the protein we provide. That is, the mosquito assumes a floral nectar rather than a host feeding mode, so neither a membrane nor heat to mimic a vertebrate host is needed. Thus, phagostimulants other than sugar and host attractants are not required for this maintenance free and reusable device. As mentioned the system is non-species specific for mosquitoes and provides comparable fecundity and fertility similar to mosquitoes grown on a blood-based diet. Finally, the system supports both male and female development and survival.

The following examples describe illustrative methods of practicing the instant invention and are not intended to limit the scope of the invention in any way.

EXAMPLES

Materials Used

Bovine serum albumin (BSA) Lyophilized powder, Bio Reagent, suitable for cell culture, ≥96% and albumin from chicken egg white powder, 62-88% (agarose gel electrophoresis) were obtained from Sigma Aldrich, St. Louis, Mo.

General Method

A blood-free diet was prepared by dissolving a protein source (2-4 g) and a carbohydrate source (1.0 g) in 20 mL amount of water (pH 7.0) or 1 mM Phosphate Buffer Saline solution (PBS) (pH 7.2) by first mixing the components and shaking the mixture well. The resultant blood-free diet was ready to use once the foam developed during shaking dissipates.

A diet feeding system as shown in FIG. 9 was used in the following examples. Each experiment was conducted with a cohort of 10 or 15 females with three replicates, unless otherwise mentioned. Three types of mosquitoes were used: *Aedes albopictus* females; *Culex pipiens molestus* females; and *Anopheles quadrimaculatus* females. The mosquitoes were provided with diet for 24 h and the diet was replenished periodically and observed for feeding at an interval of 30 minutes, unless otherwise mentioned All the experiments on blood-free diet for attraction, feeding or oviposition were carried out under room temperature (25° C.±1) and 16 h light and 8 h dark photoperiod except diapause egg experiments unless otherwise mentioned.

Figures 1A, 1B, 1C:
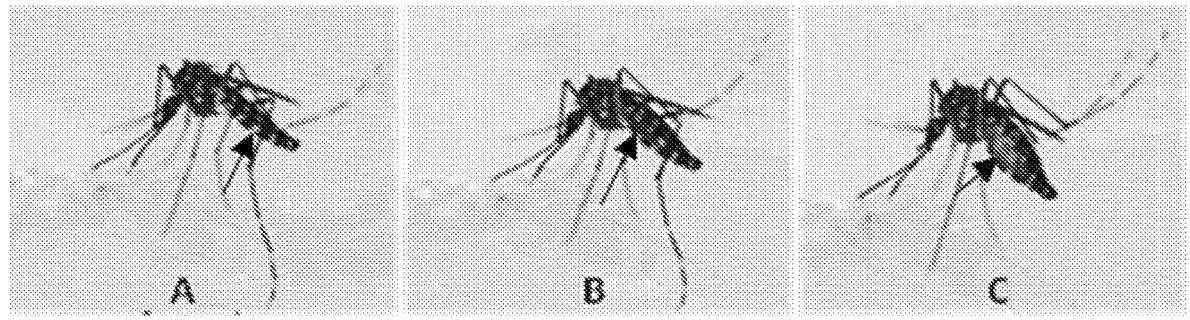
FIGS. 1A-1C shows acceptance of an exemplary blood-free diet of the present invention, by mosquito for feeding. Mosquito feeding status on new dietary system.

Experiment 1: Acceptance of proposed dietary system by mosquito for feeding:

*Aedes albopictus* females (5-7 days old) were put on fasting (by removing sugar food) for 24 h prior to acceptability test, as shown in FIG. 1A (unfed). Females were provided with exemplary artificial blood-free diet comprising BSA 10% (W/V) and Sugars 5% (W/V) in PBS for 2 hours and observed for feeding at an interval of 30 minutes. The experiment was conducted in a cohort of 10 females with three replicates. After feeding Females exhibited swollen abdomens. FIG. 1B shows a half fed mosquito and FIG. 1C shows a full fed mosquito. All the females fed on exemplary blood-free diets. Arrow shows abdominal bulging after feeding on new dietary system.

Effect of Various Diet Formulations on Fecundity and Survival Rates of *Aedes albopictus* Females Experiment 2: Fecundity of *Aedes albopictus* females fed on various diet formulations.

Mosquitoes were fed on different diets containing bovine serum albumin, cholesterol, adenosine triphosphate, sugar and their combinations, as shown in Table 1 and on Guinea pig for blood feeding. Each treatment contains a group of 10 females per replicate and experiment was repeated three times.

TABLE 1

| Sample | | Composition |
|---|---|---|
| Control 1 | Blood | blood fed on Guinea pig |
| Ex. 2.1 | BS | 20% (W/V) BSA + 5% (W/V) Sugar in PBS |
| Ex. 2.1 | BCS | 20% (W/V) BSA + 0.2% (W/V) Cholesterol + 5% (W/V) Sugar in PBS |
| C.E. A.1 | BAS | 20% (W/V) BSA + 100 mM ATP + 5% (W/V) Sugar in PBS |
| C.E. A.2 | BACS | 20% (W/V) BSA + 100 mM ATP + 0.2% (W/V) Cholesterol + 5% (W/V) Sugar in PBS |

Figure 2:
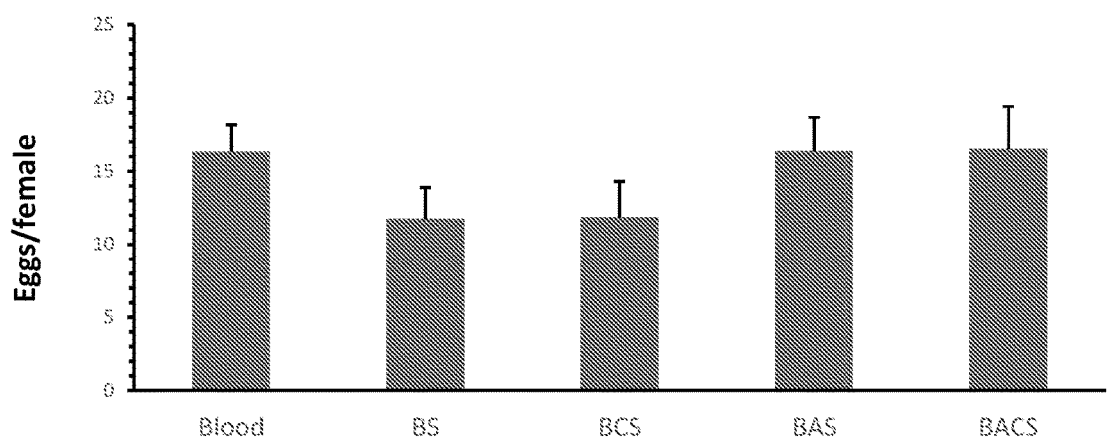
FIG. 2 shows fecundity of *Aedes albopictus* after feeding on various diets: Blood-guinea pig, BS (Bovine serum albumin (BSA) & sugar), BCS (BSA, sugar & cholesterol), BAS (BSA, ATP & sugar), and BACS (BSA, ATP, sugar & cholesterol).

FIG. 2 shows that the exemplary diets, Ex. 2.1 (BS) and 2.2 (BCS), showed similar fecundity to blood feeding on the live animal (control) and other comparative diets, C.E. A.1 (BAS) and A.2 (BACS)) comprising phagostimulant ATP (FIG. 2).

Experiment 3: Survival rate of females *Aedes albopictus* on various diet formulations:

*Aedes albopictus* females (5-7 days old) in a cohort of 15 were fed on different diet formulations, given in Table 1, after 24 h fasting. For control, fifteen females were blood fed on Guinea pig. Female survival recorded twice a week.

Figure 3:
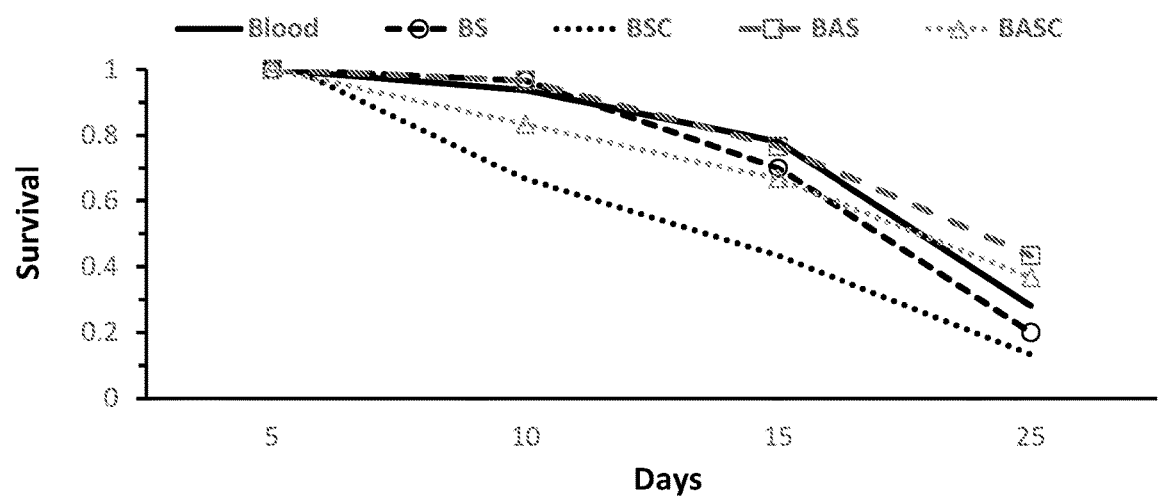
FIG. 3 shows survival of *Aedes albopictus* after feeding on various diets: Blood-guinea pig, BS (Bovine serum albumin (BSA) & sugar), BCS (BSA, sugar & cholesterol), BAS (BSA, ATP & sugar), and BACS (BSA, ATP, sugar & cholesterol).

FIG. 3 shows that the exemplary diet, Ex. 2.1 (BS) showed similar survival to blood feeding on the live animal (control 1) and other comparative diets, C.E. A.1 (BAS) and A.2 (BACS)) comprising phagostimulant ATP (FIG. 2). However, the exemplary diet Ex. 2.2 (BCS) comprising cholesterol as lipid showed unexpectedly initially high mortality.

Effect of Amount of Protein Source on Fecundity and Survival Rates of *Aedes albopictus* Females Exemplary diets comprising 2 g (10% (W/V)) or 4 g (20% (W/V)) of bovine serum albumin (BSA) as a protein source and 1 g of glucose as a sugar source, dissolved in 20 mL of PBS, were fed to 15 *Ae. albopictus* females for 24 hours.

Figure 4:
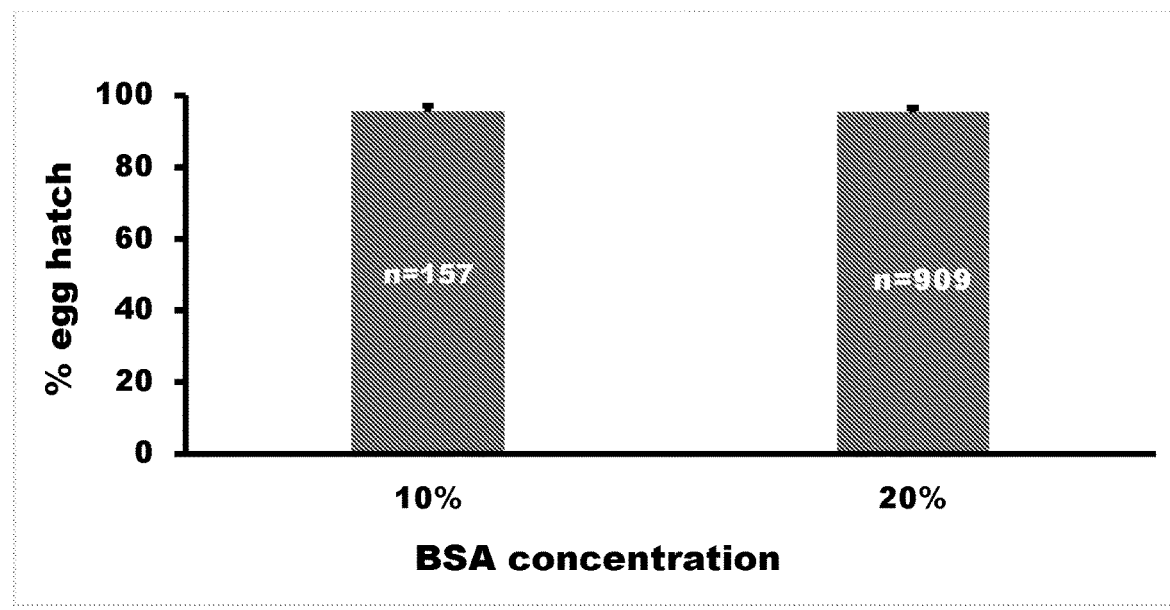
FIG. 4 shows fecundity of *Aedes albopictus* as a function of the amount of BSA in diet.

Experiment 4: FIG. 4 shows that there was no significant difference between the exemplary diets containing 10% (W/V) and 20% (W/V) concentration of bovine serum albumin (BSA).

Figure 5:
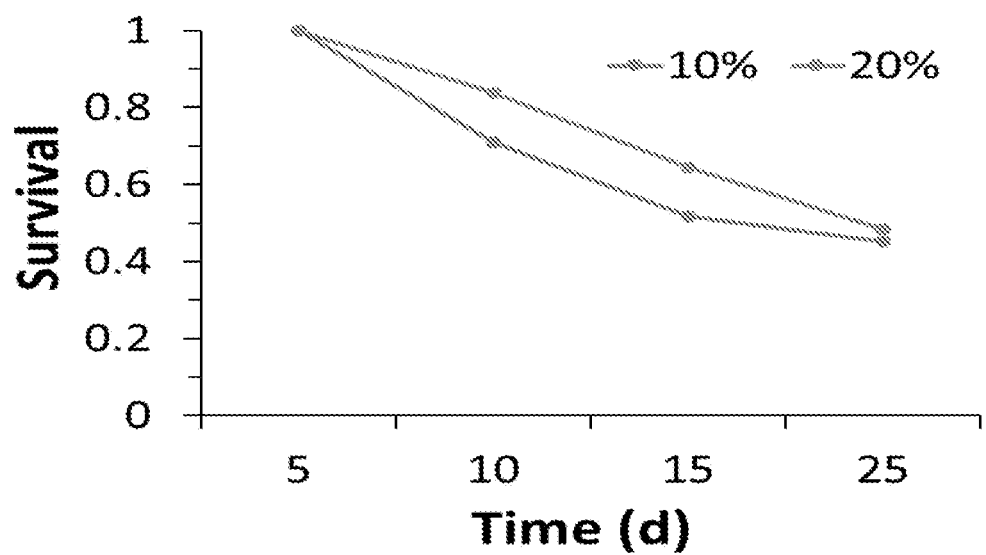
FIG. 5 shows survival of *Aedes albopictus* as a function of the amount of BSA in diet.

Experiment 5: FIG. 5 shows that there was no significant difference in adult survival between exemplary diets containing 10% (W/V) and 20% (W/V) concentrations of Bovine serum albumin.

Effect of Amount of Protein Source on Fecundity of *Aedes albopictus* Females

Experiment 6: Fecundity of *Aedes albopictus* females fed on various diet formulations compositions.

*Aedes albopictus* females (25 to 30) were fed on different diets, shown in Table 2 for 3 days after 24 h fasting. Individual females were kept into a 50 mL vial with water and oviposition paper for egg laying. After 4 days of oviposition, eggs were counted.

Table 2 summarizes various exemplary diets used:

| Sample | Composition |
|---|---|
| Control 2 | blood fed on Guinea pig |
| Ex. 3.1 | 10% (W/V) Egg Albumin + 5% (W/V) Sugar in water |
| Ex. 3.2 | 10% (W/V) Egg Albumin + 100 mM ATP + 5% (W/V) Sugar in water |
| Ex. 3.3 | 5% (W/V) Egg Albumin + 5% (W/V) Sugar in water |
| Ex. 3.4 | 5% (W/V) Egg Albumin + 5% (W/V) BSA + 5% (W/V) Sugar in water |
| Ex. 3.5 | 5% (W/V) BSA + 5% (W/V) Sugar in water |
| Ex. 3.6 | 10% (W/V) BSA + 5% (W/V) Sugar in water |

Figure 6:
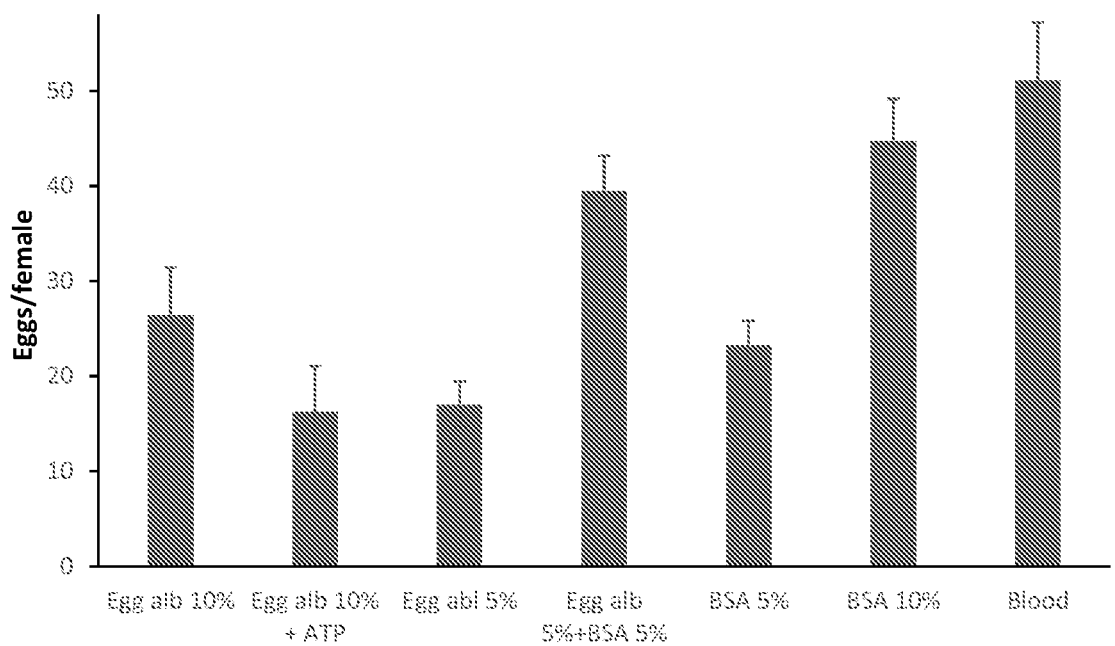
FIG. 6 shows fecundity of *Aedes albopictus* at lower concentration of various diets (Egg albo-Egg albumin, ATP-ATP, BSA-Bovine serum albumin).

FIG. 6 shows that there was no significant difference among blood, BSA (10% (W/V)) and egg albumin (5% (W/V))+BSA (5% (W/V)). It should be noted that exemplary diet Ex. 3.1 comprising 10% (W/V) egg albumin performed better than similar diet, Ex. 3.2 comprising ATP. This indicates that protein source used in this diet (BSA) can be replaced by other animal proteins such as egg albumin, which provides added benefits of cost effectiveness and less stringent storage condition requirement. Furthermore, it also indicates that the sugar phagostimulant can also work with other protein sources and with mixtures of other protein sources and BSA.

Effect of Adenosine Triphosphate (ATP) as Phagostimulant in the Exemplary Diets on Fecundity of *Aedes albopictus* Females Experiment 7: Blood-free blood-free diet is effective in the absence of phagostimulant (Adenosine triphosphate (ATP)): Two diet formulations were prepared with and without ATP, summarized below in Table 3. We compared both diets with blood.

Table 3 summarizes various exemplary diets used:

| Sample | Composition |
| --- | --- |
| Control 3 | blood fed on Guinea pig |
| Ex 4.1 | 10% (W/V) BSA + 5% (W/V) Sugar in water |
| Ex. 4.2 | 10% (W/V) BSA + 100 mM ATP + 5% (W/V) Sugar in water |

Figure 7:
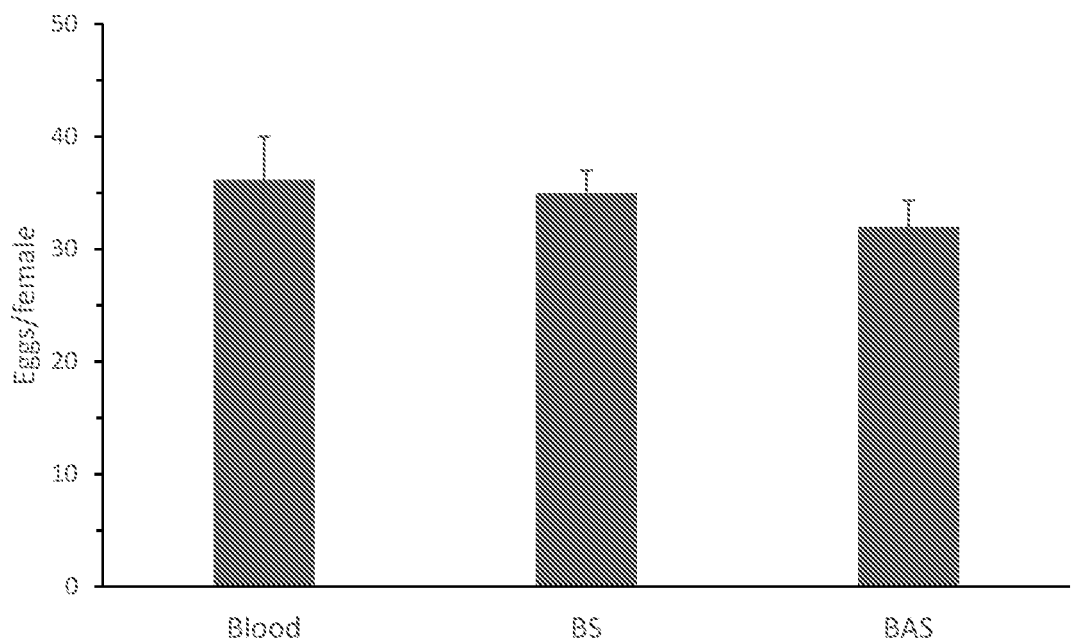
FIG. 7 shows fecundity of *Ae. albopictus* females fed on diets containing phagostimulant (Adenosine tri phosphate) and without phagostimulant against. (Blood-guinea pig, BS-Bovine serum albumin & sugar, BAS-Bovine serum albumin, ATP)

FIG. 7 shows that blood-free diet Ex. 4.1 comprising BSA and sugar only works similar to blood control and another exemplary diet, Ex. 4.2 comprising ATP in addition to BSA and sugar, indicating that inclusion of ATP as a phagostimulant is not required in the diet formulations of the present invention.

Effect of Exemplary Diet on the Fecundity of *Culex pipiens molestus* Against Control (Sugar Solution)

Figure 8:
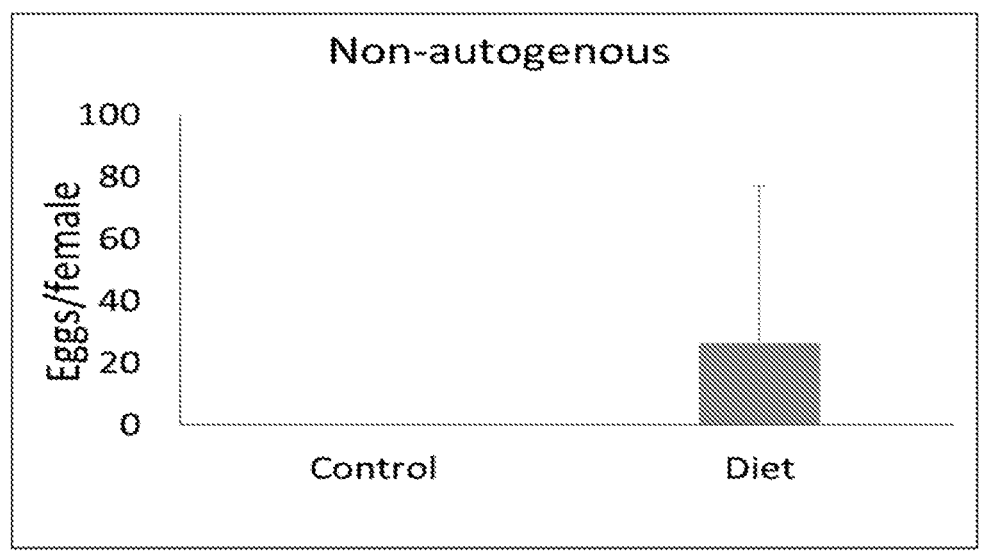
FIG. 8 shows fecundity of *Culex pipiens molestus* after feeding on blood-free diet (BS-Bovine serum albumin & sugar) against control (sugar solution).

Experiment 8: Fecundity of *Culex pipiens molestus* females fed on a blood-free diet containing BSA (20% (W/V)) & Sugar (5% (W/V)) in water. This mosquito is an autogenous, in that the first batch of eggs is laid without blood feeding. Females which have already laid first batch eggs were fed on blood-free diet and observed for oviposition. Twenty females were fed on diet formulation and observed for egg laying. Notably, eggs were also laid with blood-free diet. The control group did not lay eggs which show this species can be maintained for multiple gonotrophic cycles (FIG. 8).

Efficacy of Exemplary Diets Containing 10% (W/V) and 20% (W/V) BSA with 5% (W/V) Sugar to Support Multiple Generations of *Aedes albopictus* Mosquitoes in Comparison to Live Guinea Pig Feeding Experiment 9: Efficacy of blood-free diets containing 10% (W/V) and 20% (W/V) BSA with 5% (W/V) sugar to support multiple generations of *Aedes albopictus* mosquitoes in comparison to live Guinea pig feeding.

Initially, 50 females were taken in three groups (i.e. Blood, BSA (10% (W/V)) and BSA (20% (W/V))). One group was blood fed on Guinea pig, and the rest of the two groups were fed on exemplary diets having BSA (10% (W/V)) and 5% sugar or BSA (20% (W/V)) and 5% sugar, respectively. After feeding, fed and unfed females were sorted out and fed females were transferred to oviposition vial individually and observed for egg laying. Sugar solution (5% (W/V)) in cotton wicks was provided for survival. After 1 week of diet feeding, the females were observed for oviposition and number of eggs were counted for individual females.

Later, eggs were kept for hatching in 400 mL plastic cups and percent egg hatching rate was calculated. Hatched larvae were reared as described in Gaugler et al 2012. Brewer's yeast was provided as larval food. After pupation, pupae were transferred to 1 cu. feet mosquito cages for adult emergence and number of successful adult emerged were counted. For subsequent generations experiment, 50 females were taken and fed on blood-free dietary system and further assessed for oviposition, egg laying and larval development as described above for 10 generations. To compare the efficacy of the exemplary blood-free diets of the present invention, a control sample of blood feeding mosquitoes was taken from standard laboratory colony in each generation and were fed on Guinea pig.

Figure 10:
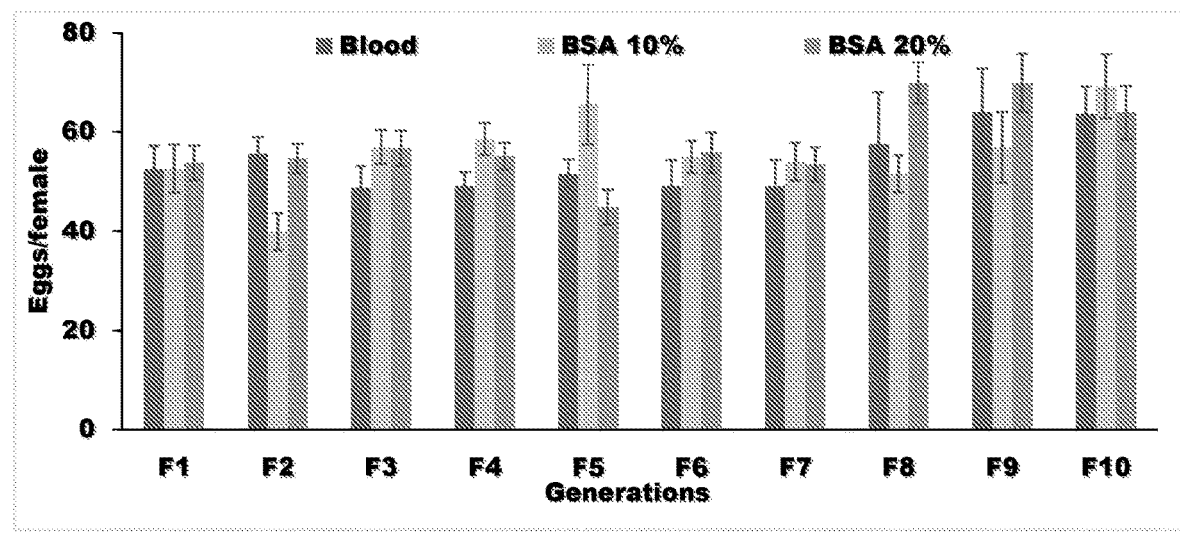
FIG. 10 shows efficacy of blood-free diets containing 10% (W/V) and 20% (W/V) BSA with 5% (W/V) sugar to support multiple generations of *Aedes albopictus* mosquitoes in comparison to live Guinea pig feeding.

FIG. 10 shows that exemplary blood-free diets can support mosquito egg production for multiple generations in the lab colony and no differences were observed at the $10^{th}$ generation with respect to egg production per female among various diets.

Preference of Exemplary Blood-Free Diets Prepared with Distilled Water or a PBS Buffer to Females *Aedes albopictus*.

Figure 11:
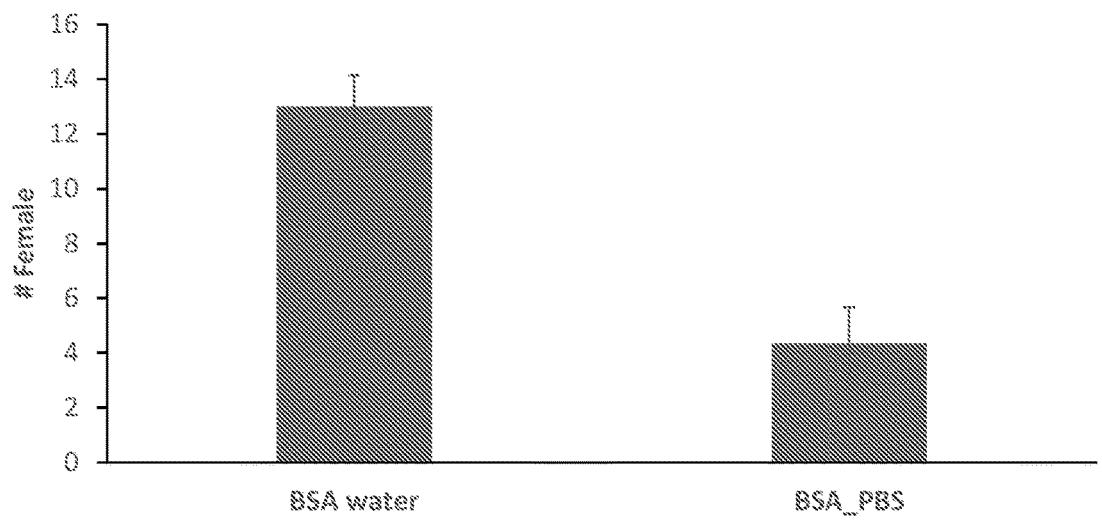
FIG. 11 shows preference of blood-free diets prepared with distilled water and a PBS buffer to females *Aedes albopictus*.

Experiment 10: FIG. 11 shows that exemplary blood-free diet prepared with BSA (10% (W/V)) in distilled water was consumed by more *Aedes albopictus* females in comparison to the diet prepared with BSA (10% (W/V)) in PBS buffer. This indicates that the exemplary blood-free diets of the present invention do not need PBS buffer and can be simplified further.

Effect of Exemplary Blood-Free Diets Prepared with Distilled Water or a PBS Buffer on Fecundity of *Aedes albopictus* Females Experiment 11: Blood-free diet prepared in distilled water (BSA 10% (W/V)+Sugar 5% (W/V) and BSA 20% (W/V)+Sugar 5% (W/V)) produced more net and gross egg per *Aedes albopictus* female in comparison to diet prepared in PBS buffer (BSA 10% (W/V)+Sugar 5% (W/V) and BSA 20% (W/V)+Sugar 5% (W/V)).

During oviposition, few females died after laying eggs and it was unclear if they died after complete or partial egg laying. Hence, gross data shows eggs from all the females (live and dead), whereas, net data shows the egg number where females were alive at the time of egg counting.

Figure 12:
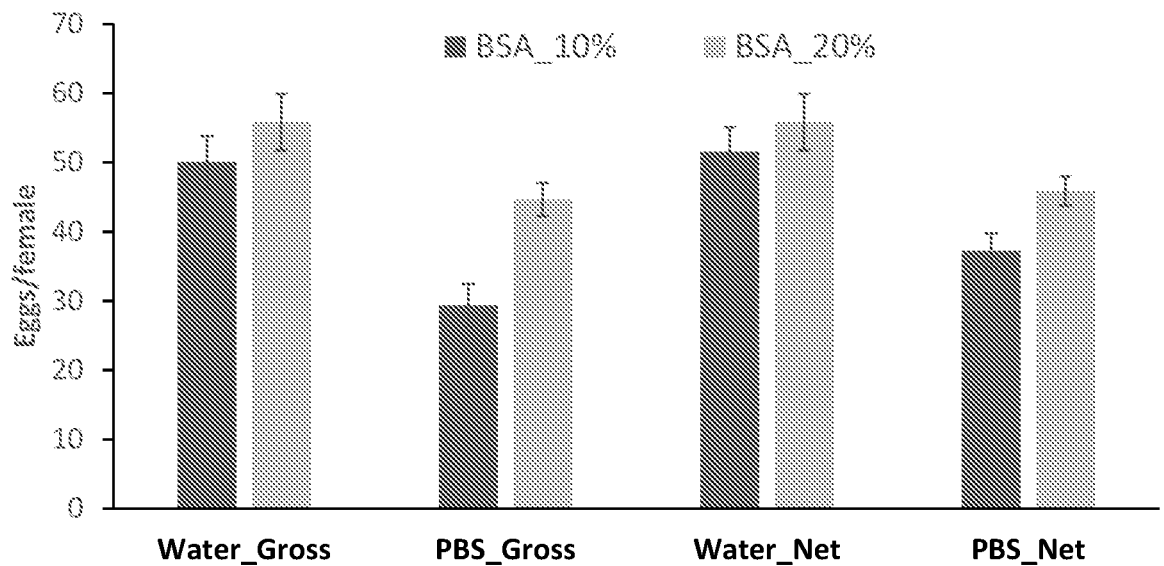
FIG. 12 shows *Aedes albopictus* egg production efficacy of blood-free diets (BSA 10% (W/V)+Sugar 5% (W/V)) and (BSA 20% (W/V)+Sugar 5% (W/V)) prepared in distilled water and PBS buffer.

FIG. 12 shows that that the presence of water of PBS in the exemplary blood-free diets does affect the fecundity of *Aedes albopictus* females. Hence, the exemplary blood-free diets of the present invention do not require PBS buffer. Thus, the use of water in the exemplary blood-free diets of the present invention instead of PBS further simplifies the diet composition, making it cost effective and readily applicable to field conditions.

Effect of Exemplary Blood-Free Diets Prepared with Distilled Water on Fecundity, Gross and Net Production of Egg Per *Aedes albopictus* Female after 24 h, 48 h and 72 h Feeding Durations.

Experiment 12: Efficacy of blood-free diet as gross and net production of egg per *Aedes albopictus* female after 24 h, 48 h and 72 h feeding durations.

Females were provided with blood-free diet (BSA (10% (W/V)) and sugar (5% (W/V))) for different time intervals i.e. 24 h, 48 h and 72 h. After the specified duration of time, mosquitoes were provided with 5% (W/V) sugar solution in cotton wick. After 4 days, all females were transferred to oviposition vial individually and observed for egg laying.

Figure 13:
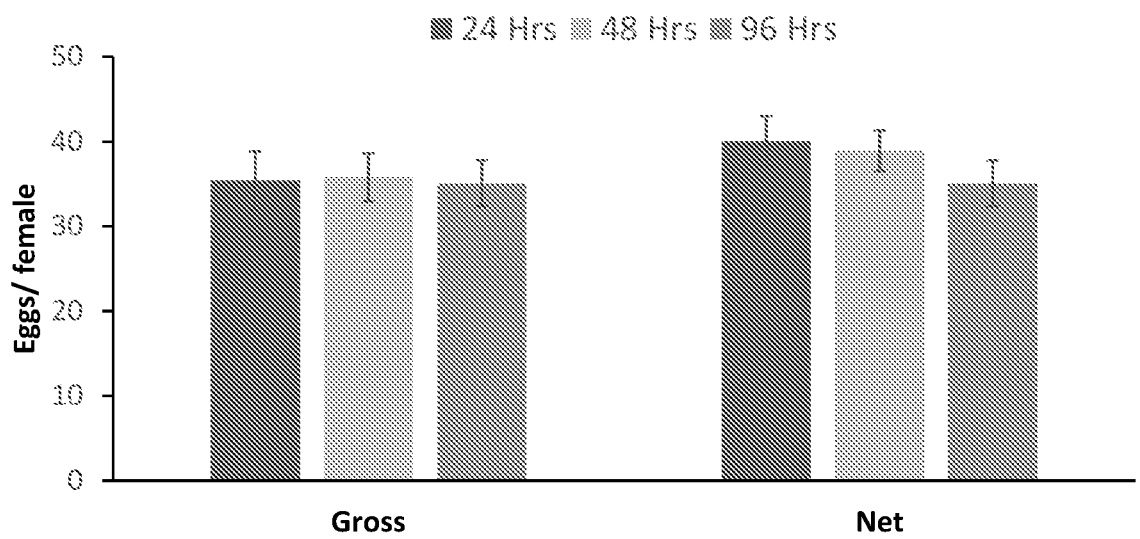
FIG. 13 shows efficacy of blood-free diet as gross and net production of egg per *Aedes albopictus* female after 24 h, 48 h and 72 h feeding durations.

FIG. 13 shows that exemplary blood-free diet can produce similar eggs with less feeding time (24 h) in comparison to longer feeding time (72 h), suggesting that extended feeding time such as 48 or 72 hours does not increase the egg production, and therefore, 24 hour feeding time is sufficient.

A Bi-Choice Experimental Set Up

Experiment 13: A Bi-choice Experimental Set Up

Figure 14A:
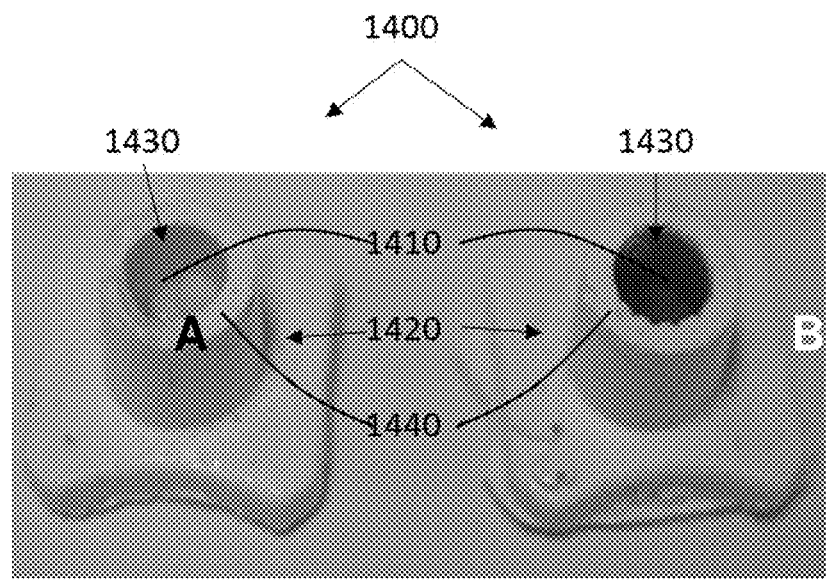
FIGS. 14A-14C shows a bi-choice experimental setup developed for the estimation of feeding preferences using UV dyes (blue and red).
Figure 14B:
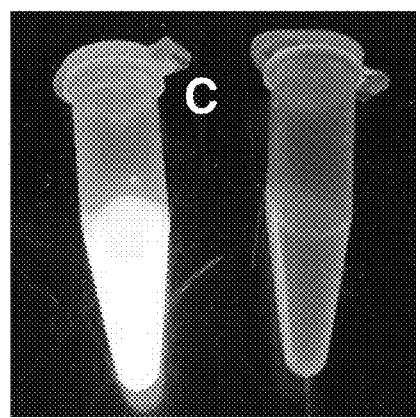
Figure 14C:
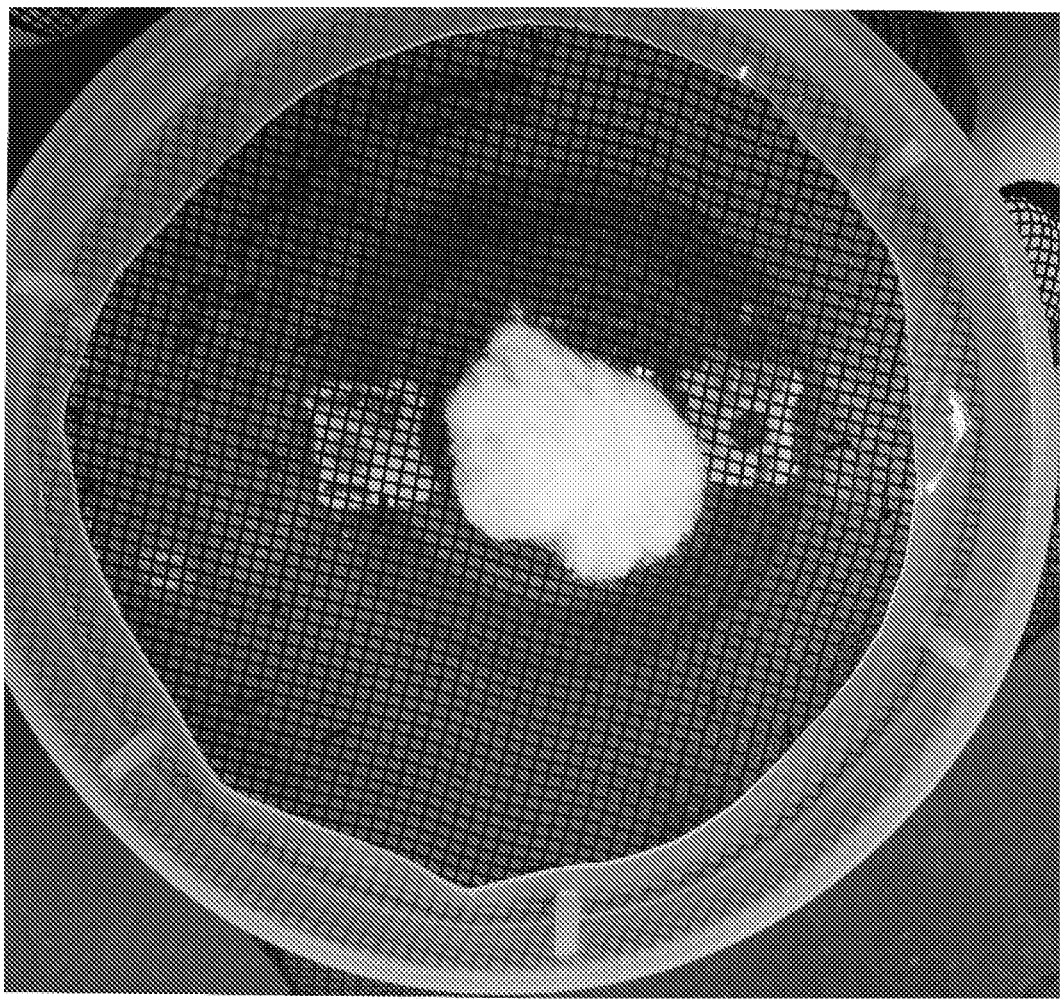

FIGS. 14A-14C show an experimental setup developed for the estimation of feeding preferences using UV dyes (blue and red): FIG. 14A shows an artificial feeding system (1400) comprising feeding devices (1420) with flat base, a diet reservoir (1420) for holding diet (1410) and a feeding platform (1440); FIG. 14B shows centrifuge tubes comprising exemplary diets with blue and red dyes, illuminated under UV light; and FIG. 14C shows a cup holding hungry mosquitoes and two diet feeders one with an exemplary diet comprising a red dye and the other with a blue dye. The red and blue dyes were mixed in the exemplary blood-free diets at 0.01% (W/V) concentrations.

Figure 15A:
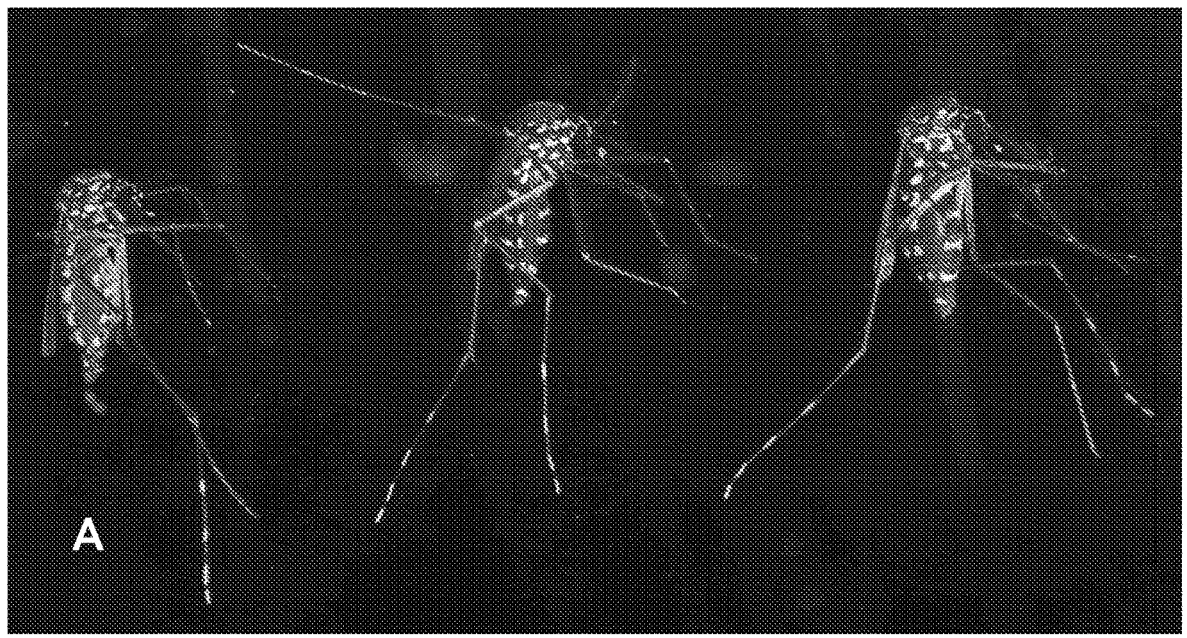
FIGS. 15A-15B shows detection of mosquito preference for diet and its components marked with blue and red dyes using the bi-choice experimental setup of FIG. 14 setup.
Figure 15B:

Experiment 14: FIG. 15 shows detection of mosquito preference for diet and its components marked with blue and red dyes using experimental setup, as shown in FIGS. 14A-14B. FIG. 15A shows mosquito fed on diets with dyes under normal daylight and FIG. 15B shows similar mosquitoes under UV light (Left side—fed on blue dye diet, Center—fed on red dye diet, Right side (referred to as mix)—fed on both blue and red dye diets). Choice experiment was tested for biases using the reciprocal exchange of sugar and BSA with blue and red dyes. We found no biases in the system for any component.

Figure 16:
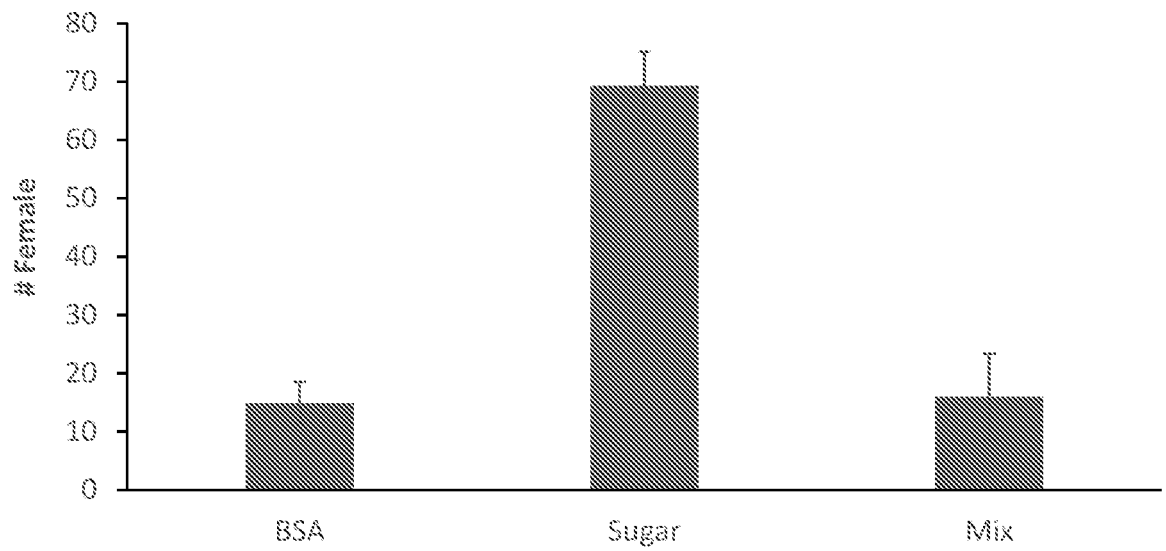
FIG. 16 shows results of a bi-choice experiment for preference of diets: sugar (5% (W/V)), BSA (10% (W/V) in water) and mix diet (where females were fed both sugar and BSA) using UV dye as in FIGS. 14 & 15.

A Bi-Choice Experiment for Preference of Sugar (5% (W/V)) against BSA (10% (W/V)) by *Aedes albopictus* Mosquitoes Experiment 15: A Bi-choice experimental set as described hereinabove was used to determine preference of sugar (5% (W/V) in water) against BSA (10% (W/V) in water). FIG. 16 shows that BSA is less preferred in comparison to sugar. Fifteen percent mosquitoes choose both sugar and BSA.

A Bi-Choice Experiment for Preference of Sugar (5% (W/V)) Against Exemplary Blood-Free Diet Comprising BSA and Sugar by *Aedes albopictus* Mosquitoes Experiment 16: A Bi-choice experimental set as described hereinabove was used to determine preference of sugar (5% (W/V)) against an exemplary diet comprising BSA (10% (W/V))+sugar (5% (W/V)) in water.

Figure 17:
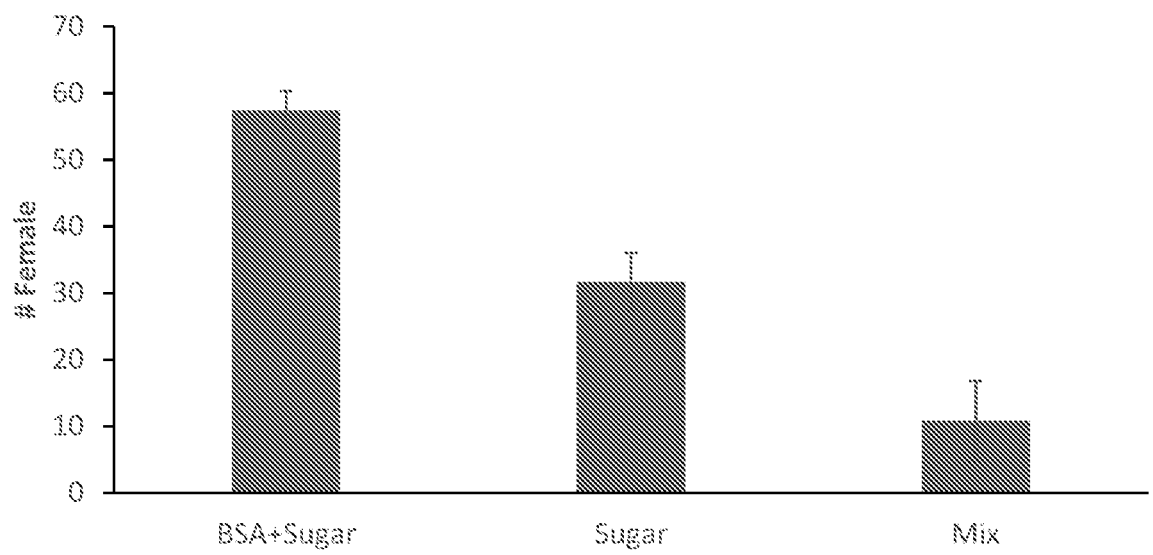
FIG. 17 shows results of a bi-choice experiment for preference of diets: sugar only diet (5% (W/V)), BSA and sugar diet (BSA (10% (W/V))+sugar (5% (W/V))) in water, and mix diet (where females were fed both sugar only and BSA+sugar diets) using UV dye as in FIGS. 14 & 15.

FIG. 17 shows a surprising result that BSA exhibits an additive effect in combination with sugar, as demonstrated by an increased preference of BSA+sugar by mosquitoes in comparison to sugar alone. Ten percent mosquitoes chose both sugar and BSA+sugar.

Preference and Efficacy of Exemplary Blood-Free Diet on Fecundity of *Anopheles quadrimaculatus*

Experiment 17. Experimental setup was exactly the same as described hereinabove. Twenty females were provided proposed diet (BSA 20% (W/V) and sugar 5% (W/V)) for 24 hours and twenty females were fed on Guinea pig as control. After feeding, females were individually transferred to 450 mL plastic cup having smaller cups filled with 30 mL water for egg laying. Females were provided with 5% (W/V) sugar solution. After 7 days, individual females were observed for egg laying and eggs were counted.

Figure 18:
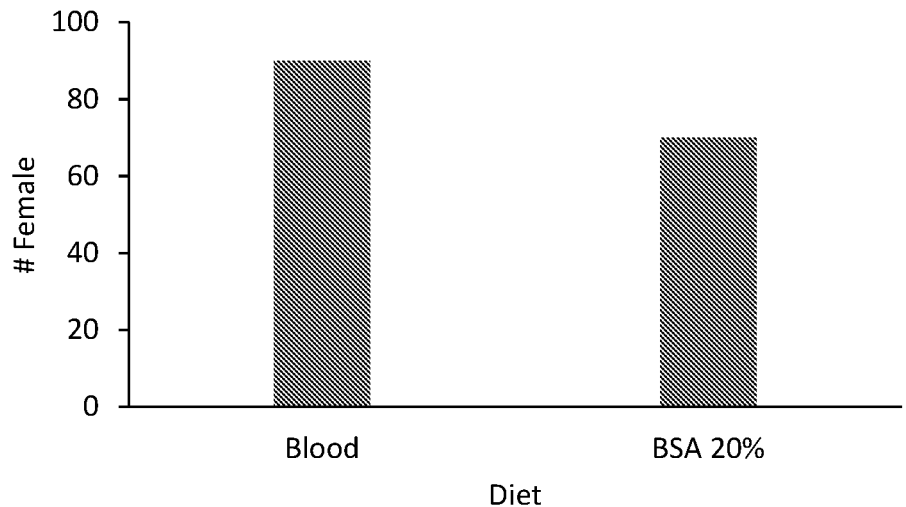
FIG. 18 shows feeding preference of a blood-free diet (BSA (20% (W/V))+sugar (5% (W/V))) in comparison to a live animal blood feeding to *Anopheles quadrimaculatus*.
Figure 19:
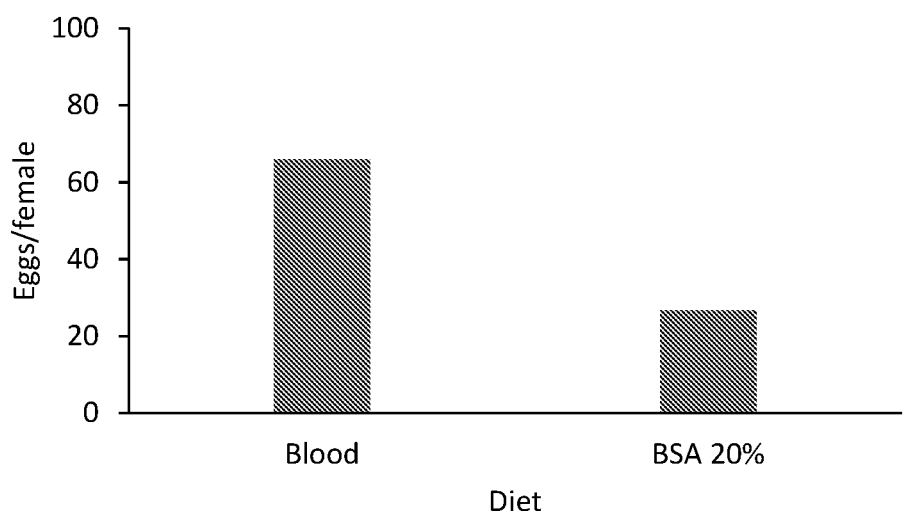
FIG. 19 shows egg laying efficacy of *Anopheles quadrimaculatus* fed on blood-free diet (BSA 20% (W/V)+Sugar 5% (W/V)) and on a live animal for blood.

FIG. 18 shows that exemplary diet comprising BSA 20% (W/V) and Sugar 5% (W/V) in water is similar in preference to feeding on blood by *Anopheles quadrimaculatus*. FIG. 19 shows egg production efficacy of the exemplary diet in comparison to blood.

Preference and Efficacy of Exemplary Blood-Free Diet on Fecundity of *Aedes albopictus* for Diapause Egg Production in Short Day Photoperiod (8 h)

Figure 20:
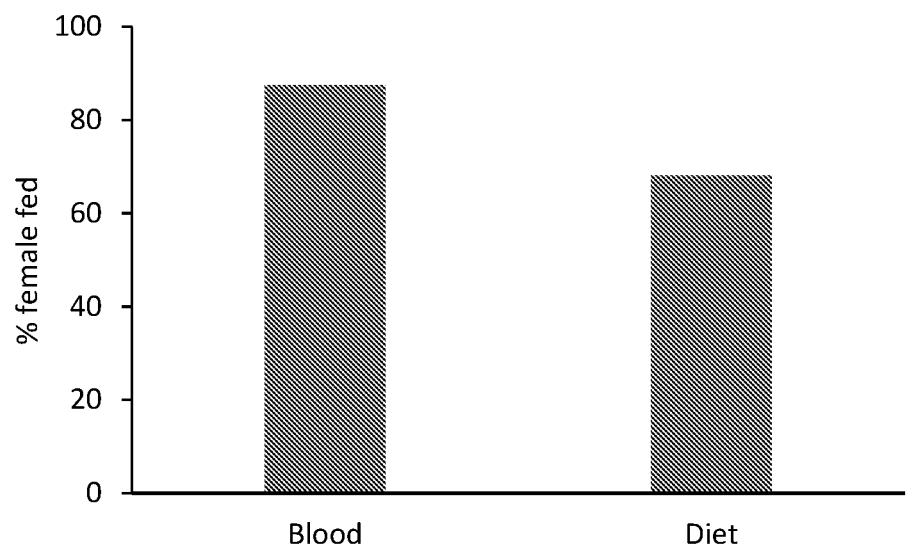
FIG. 20 shows preference of blood-free diet and a live animal blood feeding by diapausing *Aedes albopictus* females under short day photoperiod (8 h) and lower temperature (21° C.) conditions.
Figure 21:
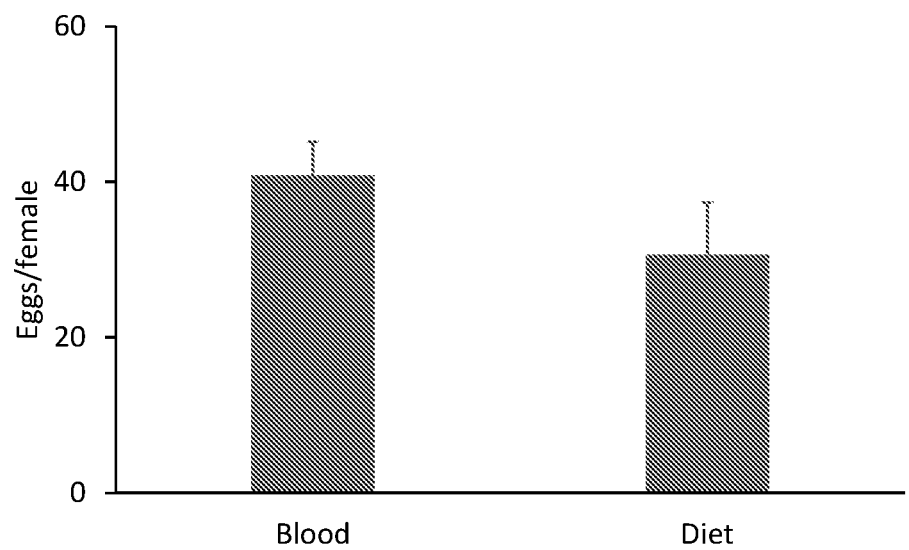
FIG. 21 shows efficacy of blood-free diet and a live animal blood feeding on *Aedes albopictus* diapause egg production under short day photoperiod (8 h) and lower temperature (21° C.).

Experiment 18. Efficacy of blood-free diet (BSA 20% (W/V)+Sugar 5% (W/V)) for the production of *Aedes albopictus* diapause eggs at short day photoperiod (8 h) and lower temperature (21° C.) to produce diapause eggs in comparison to live animal blood feeding. FIG. 20 shows that exemplary diet was readily accepted by mosquitoes reared under diapausing condition. FIG. 21 shows that females lay diapause eggs under the same conditions and the egg production efficacy of the exemplary diet was similar in comparison to blood.

Pitts (2014) is perhaps the nearest diet to the exemplary blood-free diet, as disclosed hereinabove.

Pitts (2014) diet comprises BSA (200 mg/mL) and ATP (1 mM) in PBS and in common with nearly all artificial mosquito diets, include bovine serum albumin (BSA) as a blood-replacement protein. As with virtually all artificial mosquito diets, Pitt's system requires ATP as a phagostimulant, as well as a feeding device with heating, and a membrane, all of which are costly and complex to operate. Moreover, an odor blend of ammonium hydroxide, lactic acid, isovaleric acid, geranyl acetone, and butylamine was applied to the membrane as a host-seeking stimulant. This group of chemicals are complex to prepare, adding another obstacle to scale up. Despite this complexity, Pitts obtained good egg production from their feeding system, yet suboptimal egg hatch (71.8%) in comparison to exemplary blood-free diet described herein comprising BSA (200 mg/mL) and sugar (50 mg/mL) in water (volume made up to 1 mL) (98% egg hatch).

It will be apparent to those skilled in the art that various modifications and variations can be made in the practice of the present invention and in construction of this system without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

REFERENCES

Accar E B, Deane G F, Johanson E, Mullen E R, Myhrvold N P, Peterson N R, Tegreene C T, Whitmer C, Wood L L. 2012. Food composition for hematophagous insects. US Patent, U.S. Pat. No. 8,133,524B1

Allan S A, Bernier U R, Kline D L. 2010. Laboratory evaluation of lactic acid on attraction of *Culex* spp. (Diptera: Culicidae). J. Vect. Ecol. 35, 318-324.

Gonzales K K, Tsujimoto H, Hansen T A. 2014. Blood serum and BSA, but neither red blood cells nor hemoglobin can support vitellogenesis and egg production in the dengue vector *Aedes aegypti*. PeerJ. 3:e938.

Hosoi T. 1959. Identification of blood components which induce gorging of the mosquito. Journal of Insect Physiology. 3, 191-218.

Kogan P H. 1990. Substitute blood meal for investigating and maintaining *Aedes aegypti* (Diptera: Culicidae). J. Med. Entomol. 27, 709-712.

Phasomkusolsil S, Tawong J, Monkanna N, Pantuwatana K, Damdangdee N, Khongtak W, Kertmanee Y, Evans B P, Schuster A L. 2013. Maintenance of mosquito vectors: effects of blood source on feeding, survival, fecundity, and egg hatching rates. J. Vect. Ecol. 38, 38-45.

Pitts R J. 2014. A blood-free protein meal supporting oogenesis in the Asian tiger mosquito, *Aedes albopictus* (Skuse). J. Insect Physiol. 64, 1-6.

What is claimed is:

1. A method of maintaining and growing hematophagus insects, comprising:
   (a) providing an artificial feeding system comprising:
      i) a diet reservoir for receiving a synthetic, blood-free diet formulation;
      ii) at least one feeding platform that is hydrophobic and floats; and
      iii) an optional mosquito proof covering separating said diet reservoir from said platform, said system and diet formulation being suitable for egg production and colony maintenance, wherein said system lacks a membrane;
(b) dissolving the synthetic, blood-free diet formulation in water; and
(c) feeding the hematophagus insects with said synthetic blood free diet formulation.

2. The method of claim 1, wherein said diet reservoir is 5 mm or less in depth.

3. The method of claim 1, wherein said system comprises multiple feeding platforms.

4. The method of claim 1, wherein said covering is present and is a mesh having a pore size of about 2 mm.

5. The method of claim 1, wherein said diet reservoir is circular, square, or triangular in shape.

6. The method system of claim 1, wherein said synthetic blood free diet formulation comprises a traceable reagent.

7. The method of claim 1, wherein said traceable reagent is a UV dye.

8. The method of claim 1, wherein maintenance and growth occurs across multiple generations of mosquito.

9. The method of claim 1, wherein mosquitos are reared under diapausing conditions and produce viable diapause eggs.

10. The method of claim 1, wherein said A synthetic blood-free diet formulation comprises effective amounts of a protein source, a carbohydrate source and, optionally a lipid source, said diet being suitable for egg production and colony maintenance.

11. The method of claim 10, wherein said protein source is selected from the group consisting of animal protein, milk protein, plant protein, insect protein, arthropod protein, and amino acids.

12. The method of claim 10, wherein said protein source is bovine serum albumin and/or egg albumin.

13. The method of claim 10, wherein said carbohydrate source comprises at least one of glucose, sucrose, fructose, or mixtures thereof.

14. The method of claim 10, wherein said lipid source is present and is cholesterol.

15. The method of claim 10, wherein said synthetic blood-free diet formulation lacks an ATP phagostimulant.

16. The method of claim 10, wherein said method supports growth of mosquito species selected from *Aedes, Anopheles* and *Culex* mosquitoes.

17. The method of claim 10, wherein the protein source is present in an amount of 5-30% (W/V) and the carbohydrate source is present in an amount of 3-10% (W/V).

18. The method of claim 10, wherein the diet formulation is selected from the group consisting of:
Diet 1: Bovine Serum albumin (5-20%) (W/V) Sugar (5-10%) (W/V) Dissolved in 1 mM Phosphate Buffered Saline (pH 7.2);
Diet 2: Bovine Serum albumin (5-10%) (W/V) Egg albumin (5-10%) (W/V) Sugar (5-10%) (W/V) dissolved in 1 mM Phosphate Buffered Saline (pH 7.2);
Diet 3: Egg albumin (5-10%) (W/V) Sugar (5-10%) (W/V) dissolved in 1 mM Phosphate Buffered Saline (pH 7.2);
Diet 4: Bovine Serum albumin (5-20%) (W/V);
Sugar (5-10%) (W/V) Cholesterol (1-2 mg/ml) dissolved in 1 mM Phosphate Buffered Saline (pH 7.2); and
Diet 5: Bovine Serum albumin (5-20%) (W/V) Sugar (5-10%) (W/V) dissolved in Distilled water.

19. The method of claim 1, wherein the feeding platform is formed from a mesh.

20. The method of claim 1, wherein said method supports growth and maintenance of a mosquito colony comprising *Aedes, Anopheles* or *Culex* mosquitoes.

* * * * *